United States Patent [19]

Byars et al.

[11] 4,054,129

[45] Oct. 18, 1977

[54] SYSTEM FOR APPLYING PULSATING PRESSURE TO THE BODY

[75] Inventors: Edward F. Byars; Thomas J. Tarnay, both of Morgantown, W. Va.; Gordon R. Hopkins, Memphis, Tenn.

[73] Assignee: Alba-Waldensian, Inc., Valdese, N.C.

[21] Appl. No.: 671,029

[22] Filed: Mar. 29, 1976

[51] Int. Cl.[2] .............. A61N 1/00

[52] U.S. Cl. .............. 128/24 R

[58] Field of Search .............. 128/24 R, 25, 60, 64, 128/DIG. 20, 165

[56] References Cited

U.S. PATENT DOCUMENTS

| | | | |
|---|---|---|---|
| 2,747,570 | 5/1956 | Jobst | 128/24 R |
| 3,872,862 | 3/1975 | Hume | 128/165 |

FOREIGN PATENT DOCUMENTS

| | | | |
|---|---|---|---|
| 735,700 | 6/1966 | Canada | 128/DIG. 20 |
| 836,549 | 4/1952 | Germany | 128/64 |

*Primary Examiner*—Lawrence W. Trapp

*Attorney, Agent, or Firm*—Bell, Seltzer, Park & Gibson

[57] ABSTRACT

The system includes a stocking for stimulating fluid flow within the leg of the wearer to thereby reduce the likelihood of venous thrombosis during surgery, post-operative recovery periods, and during other periods of inactivity. The stocking is easy to apply and remove, is lightweight and comfortable for wear by bed patients or ambulant patients. The stocking includes a seamless knitted leg which is fashioned to generally conform to the configuration of the leg on which the stocking is to be placed and is sufficiently stretchable to permit easy placement and removal but is otherwise substantially unstretchable. A longitudinally extending pocket is provided along the front portion of the leg and covers substantially one-half the circumferential surface of the leg with an expandable bladder generally conforming to the size of the pocket and positioned within the pocket. The system also includes pumping means for periodically expanding the bladder to exert direct pressure against the front of the leg and to circumferentially contract the remainder of the leg of the stocking to stimulate the fluid flow in the leg of the wearer.

18 Claims, 6 Drawing Figures

SYSTEM FOR APPLYING PULSATING PRESSURE TO THE BODY

This invention relates generally to a system for applying pulsating pressure to the body and includes stockings for intermittently applying pressure to the legs in order to stimulate fluid flow within the legs of the wearer and to thereby reduce the likelihood of venous thrombosis. More specifically, the stocking includes a seamless knitted leg portion which is fashioned to generally conform to the configuration of the leg of the wearer and is of relatively lightweight construction so that the stocking is comfortable for wear by a bed patient or an ambulant patient.

It has been recognized that surgery and other types of bed patients are particularly susceptible to venous thrombosis. Various types of pneumatic leggins, boots, pressure chambers and the like have been proposed for periodically compressing and releasing the legs of the wearer to accelerate blood flow. However, such prior devices have disadvantages which have prevented their widespread use. In many instances, these prior devices have been heavy and cumbersome, thereby preventing or at least limiting ambulation and other movement of the bed patient. The pressure applying means extends completely around the legs of the wearer in many of these prior devices and this could actually operate to limit blood circulation in the patient.

In an apparent attempt to overcome these disadvantages, it has been proposed in the Jobst U.S. Pat. No. 2,747,570 to provide an envelope surrounding the leg of the patient with an inflatable tube, or a pair of tubes, extending up one side of the envelope. When the tube is expanded, direct inward pressure is applied against the area of the leg covered by the tube. However, the inflatable tube is of a relatively small diameter so that it engages only a small area of the circumference of the leg of the wearer and may apply so much pressure in such a small area as to be uncomfortable and may restrict blood circulation or may cause localized tissue damage.

With the foregoing in mind, it is an object of the present invention to provide a system for applying pulsating pressure to the body for stimulating fluid flow within the body and to thereby reduce the likelihood of venous thrombosis. The system includes an appliance adapted to encompass a portion of the body, such as stockings to be worn on the legs. The stockings are easy to apply and remove and are lightweight and comfortable for wear by bed patients or ambulant patients in the hospital or in the home. The stocking includes a seamless knitted leg which is fashioned to generally conform to the configuration of the leg of the wearer. A longitudinally extending pocket is provided in the leg of the stocking with an expandable bladder positioned in the pocket. The system also includes pumping means for periodically expanding the bladder to exert direct pressure against the portion of the leg covered thereby and to circumferentially contract the remaining corresponding portion of the leg to stimulate fluid flow in the corresponding portion of the leg. The bladder is centered on the front of the leg and covers approximately one-half the circumference of the stocking so that the front portion of the leg is subjected to direct pressure when the bladder is expanded while the rear portion of the leg is subjected to a contracting pressure as the stocking tightens around the leg.

In accordance with the present invention, the pocket extends longitudinally along the front of the leg and from at least adjacent the ankle of the wearer to a position immediately below the knee and extends widthwise substantially half the circumference of the leg. The expandable bladder is positioned in the pocket and may be easily connected and disconnected to the pumping means for periodically expanding the bladder to exert pressure against the leg of the wearer. The pocket includes an outer layer formed by the seamless knitted leg portion of the stocking and an inner layer formed of a substantially rectangular piece of fabric positioned inside of the leg and being sewn on three sides to the leg of the stocking with one end being open to permit easy placement and removal of the expandable bladder in the pocket. The substantially rectangular piece of fabric forming the inner layer of the pocket prevents the bladder from direct engagement with the leg and is provided with inwardly extending terry loops to provide a soft cushion against the leg of the wearer.

Other objects and advantages will appear as the description proceeds when taken in connection with the accompanying drawings, in which.

Although the pressure applying system of the present invention is illustrated and described as including an appliance in the form of a pair of stockings with seamless knitted leg and foot portions adapted to fit the legs of the wearer, it is to be understood that the system may include another type of appliance which includes a seamless knitted sleeve adapted to generally conform to the configuration of other portions of the human body, such as the arm, trunk, etc. The stocking includes a seamless knitted leg portion 10 formed on a circular hosiery knitting machine with fashioning to gradually reduce the size of the stitch loops so that the leg portion 10 generally conforms to the configuration of the leg.

Figure 2:
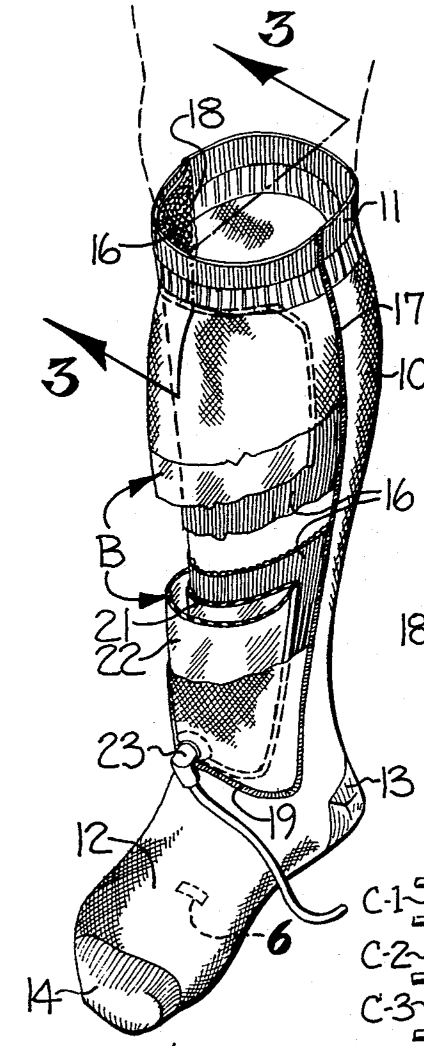
FIG. 2 is an enlarged isometric view, with parts broken away, of one of the stockings as it would appear on the leg.
Figure 6:
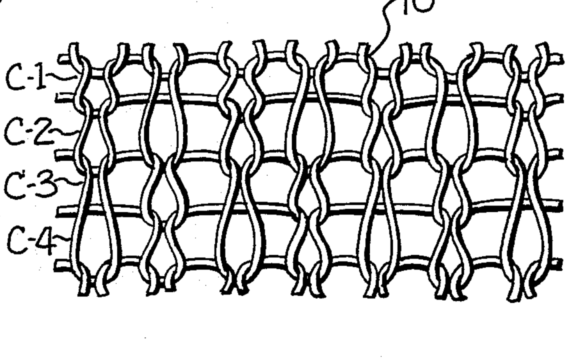
FIG. 6 is a greatly enlarged view of a small fragmentary portion of the knit fabric forming the leg and foot of the stocking, being taken in the dotted line area 6 in FIG. 2.

The leg portion 10 is preferably knit from the top downwardly in FIG. 2 and includes an upper cuff portion 11, illustrated in the form of a turned welt with spandex yarn incorporated therein, to aid in supporting the upper end of the stocking. The leg portion 10 is sufficiently stretchable to permit easy placement and removal of the stocking on the leg but is otherwise substantially unstretchable and is preferably knit of a non-stretchable yarn in a knit and float stitch construction, such as illustrated in FIG. 6. This stitch construction provides an open mesh appearance to provide ventilation and limits the stretchability of the leg portion. The stocking is relatively sheer and is knit of non-stretchable yarn, such as nylon, within the range of about 50 to 300 denier. It has been found that a satisfactory stocking can be produced by utilizing 100 denier nylon in the leg portion 10. As will be recognized, the alternate courses C-1 and C-3 have stitch loops formed in every wale while the intervening courses C-2 and C-4 have stitch loops formed in every other wale with the yarn being floated across the remaining wales. The floats in the course C-2 are offset relative to the floats in the course C-4.

A longitudinally extending pocket is provided in the leg portion 10 of the stocking and extends from at least adjacent the ankle of the wearer to a position immediately below the knee. However, it is to be understood that the pocket could extend down into any portion of the foot of the stocking and the stocking and pocket may extend upwardly above the knee and cover the thigh area, if desired. The stocking is provided with a foot portion 12 including a heel pocket 13 and a toe pocket 14. Toe inspection means is provided and is illustrated as an opening 15 provided adjacent the toe pocket 14 and normally extends across and beneath the toes of the wearer so that the toes of the patient may be exposed through the toe opening 15 for inspection by the doctor. The heel and toe portions 13, 14 are preferably knit in the usual manner by reciprocation of the needle cylinder while fashioned widened and narrowed gussets are formed. The heel and toe portions 13, 14 are preferably knit with plain stitch loops and may be formed of stretchable yarn.

The longitudinally extending pocket in the seamless knit leg portion 10 of the stocking should have a width which is greater than one-fourth the circumference of the leg portion 10 of the stocking but the width should be less than the entire circumference. The pocket is centered along the front of the leg portion 10 and is illustrated as encompassing substantially one-half the circumference of the leg. The pocket includes an outer layer formed by the seamless knitted leg portion 10 of the stocking and an inner layer 16 formed by a substantially rectangular piece of material, such as fabric positioned inside of the leg.

Figure 3:
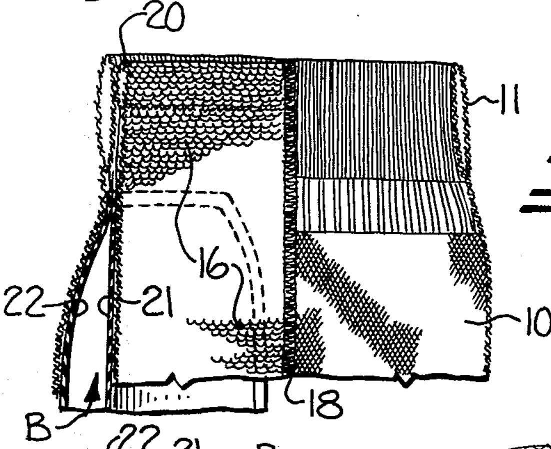
FIG. 3 is an enlarged fragmentary vertical sectional view through the upper end portion of the stocking, being taken substantially along the line 3—3 in FIG. 2.
Figure 4:
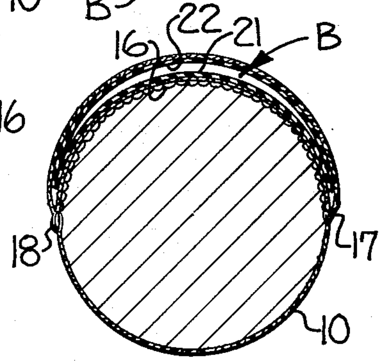
FIG. 4 is a transverse vertical sectional view taken substantially along the line 4—4 in FIG. 1 and illustrating the bladder in partially relaxed or contracted condition.

The rectangular piece of fabric forming the inner layer 16 is longer in the longitudinal direction than in the widthwise direction and seams 17, 18 connect opposite longitudinal sides of the inner layer 16 to the leg 10 while a seam 19 connects the lower end of the inner layer 16 to the leg portion 10 to form a pocket which is open at its upper end. The upper end of the inner layer 16 is preferably turned to form a welt 20 and the piece of fabric forming the inner layer 16 is knitted with terry loops provided on the inner surface, as illustrated in FIG. 3, to provide a cushion against the leg of the wearer and also absorbs moisture.

The system also includes expandable bladder means, broadly indicated at B, which generally conforms to the size of the pocket and is positioned within the pocket. The expandable bladder means B includes respective inner and outer sheets of flexible plastic material 21, 22 which are heat sealed together around the outer peripheral edges thereof. An inlet nozzle, in the form of an elbow 23 is provided at the lower end of the bladder B and passes through a small opening in the leg portion 10. The elbow 23 is communicatively connected with the space between the inner and outer layers 21, 22 of the bladder.

Of course, the bladder B may also be formed with other types of material and although it is illustrated as being substantially rectangular, the bladder may be formed in other configurations. While the bladder B is illustrated as being supported in the pocket in the stocking, it is to be understood that the bladder may be supported in the leg portion 10 of the stocking by other suitable means.

Figure 1:
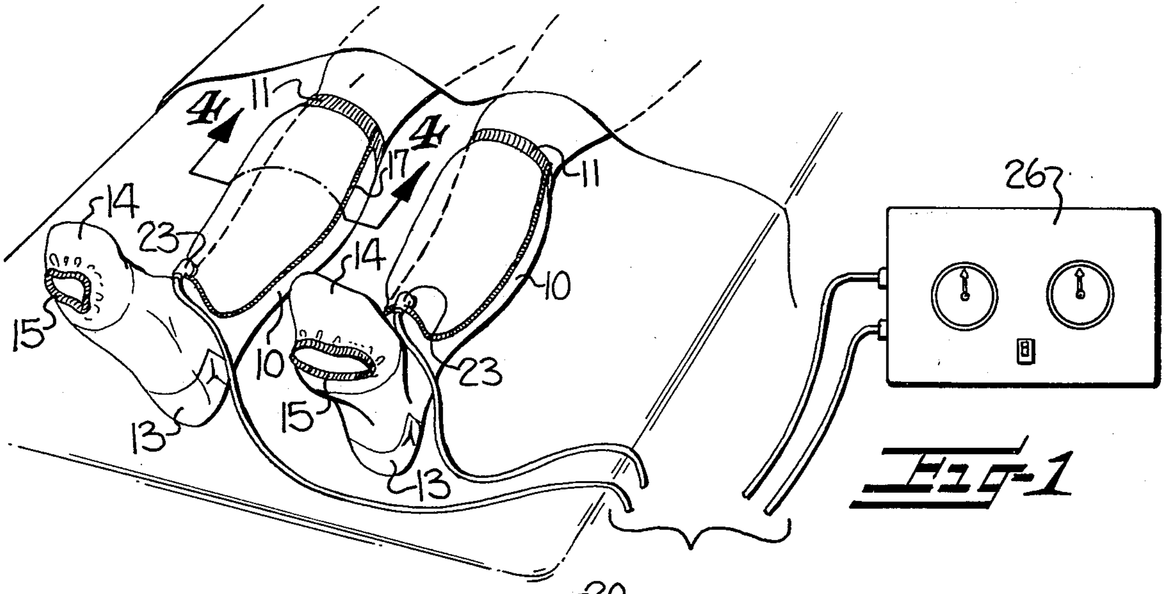
FIG. 1 is an isometric view of the pressure applying system, illustrated in the form of a pair of stockings positioned on the legs of a patient and illustrating the manner in which the stockings are connected to the pumping means for periodic expansion to apply pulsating pressure against the legs.

The system also includes pumping and control means, indicated at 26, for periodically expanding the bladders B. Lines 24, 25 are connected at one end to the pumping and control unit 26 and their other ends are connected to the bladders B in the stockings on the legs of the patient (FIG. 1). The lines 24, 25 can be disconnected from the elbows 23 so that the bladders B may be easily removed through the open upper ends of the pockets in the leg portions 10 of the stockings. The ease of removal and replacement of the bladders B permits use of the bladders in other stockings and permits laundering of the stockings without harm to the bladders.

The pumping and control unit 26 is preferably provided with suitable gauges to indicate the amount of pressure applied through the lines 24, 25 and a timing device for alternately applying pressure to each of the legs of the wearer of the stockings. The amount of pressure applied and the time cycle may be varied, depending upon the condition of the patient. Generally, it has been found that a pressure of 50 millimeters of mercury applied to one leg for a period of approximately 90 seconds and then the same pressure applied to the other leg for the next 90 second period will stimulate venous blood flow sufficiently to reduce the likelihood of venous thrombosis. While the pressure is being applied to one leg, the pressure on the other leg is released to permit the blood to be resupplied to this leg. The means for periodically expanding the bladders B in an alternating manner to exert pressure against the legs of the wearer may include a pump for pumping any type of fluid, such as air, into the bladders B.

Figure 5:
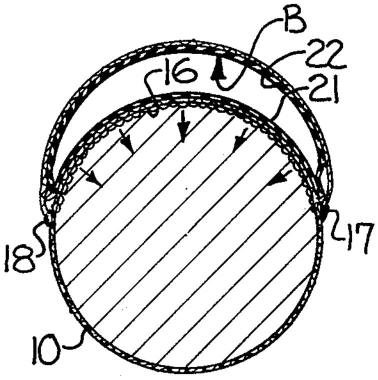
FIG. 5 is a view similar to FIG. 4 but showing the bladder in expanded position and with the stocking applying pressure to the leg of the wearer.

As illustrated in FIG. 5, when the proper amount of pressure is built up in the bladder B, direct pressure is applied against the front portion of the leg and the remaining portion of the leg portion 10 of the stocking is circumferentially contracted and maintained in a contracted condition for the desired period of time, approximately 90 seconds. When the pressure in the bladder is released, the pressure against the leg of the wearer is also released and the pressure is not again applied until the leg has had an opportunity to be resupplied with blood. This repeated cycle of expanding and contracting stimulates the venous blood flow in the legs of the wearer and thereby reduces the likelihood of venous thrombosis in the patient.

Although the system of the present invention has been described as being of particular value in stimulating fluid flow to reduce the likelihood of venous thrombosis, it is to be understood that the system also provides other benefits. For example, the application of pulsating pressure provides a massaging effect which simulates normal muscle and tissue activity which, in turn, promotes reduction of edema and release of clot dissolving substances and produces other desirable chemical changes.

The pulsating pressure applying system of the present invention is thus economically formed and is lightweight and comfortable for wear by either bed or ambulant patients. The open mesh nature of the stocking permits ventilation of the leg. The stockings may be easily connected to the pumping means for applying the required amount of pulsating pressure to the legs of the wearer. Because of the economical cost of the stockings, they may be discarded after use or the bladders may be removed from the pocket and the stockings may be laundered for reuse.

In the drawings and specification there has been set forth a preferred embodiment of the invention, and although specific terms are employed, they are used in a generic and descriptive sense only and not for purposes of limitation, the scope of the invention being defined in the claims.

That which is claimed is:

1. A system for applying pulsating pressure to a portion of the human body, said system comprising a. an appliance comprising a seamless knitted sleeve generally conforming to the configuration of the portion of the human body on which said sleeve is to be placed, said seamless knitted sleeve being sufficiently stretchable to permit easy placement and removal, b. a pocket attached longitudinally along and partially around said sleeve, the width of said pocket being greater than one-fourth the circumference of said sleeve, c. expandable bladder means positioned in said pocket and extending longitudinally of said seamless knitted sleeve, and d. means for periodically expanding said bladder to exert direct pressure against the portion of the body covered thereby and to circumferentially contract said sleeve and apply pressure to the corresponding portion of the body encompassed by said sleeve.

2. A system for applying pulsating pressure to a portion of the human body, said system comprising a. an appliance comprising a sleeve generally conforming to the configuration of the portion of the human body on which said sleeve is to be placed, b. at least one pocket longitudinally attached along said sleeve, the width of said pocket being greater than one-fourth the circumference of said sleeve but being no greater than substantially one-half the circumference of said sleeve, c. expandable bladder means generally conforming to the size of said pocket and positioned within said pocket, and d. means for periodically expanding said bladder to exert direct pressure against the portion of the body covered thereby and to circumferentially contract said sleeve and apply pressure to the corresponding portion of the body encompassed by said sleeve.

3. A system according to claim 2 wherein said longitudinally extending pocket includes an outer layer formed by said sleeve, an inner layer comprising a substantially rectangular piece of material positioned inside of said sleeve, said rectangular piece of material being longer in the longitudinal dimension than in the widthwise dimension and with the longitudinal dimension extending longitudinally of said sleeve, and seam means connecting at least opposite longitudinal sides of said piece of material to said sleeve so that said inner layer prevents direct contact by said expandable bladder means with the corresponding portion of the body of the wearer.

4. A system according to claim 3 wherein one end of said piece of material forming said inner layer of said pocket is free of connection to said sleeve to permit easy placement and removal of said expandable bladder means in said pocket.

5. A system according to claim 3 wherein said rectangular piece of material forming said inner layer of said pocket is knitted and includes terry loops extending inwardly of said sleeve and forming a moisture absorbing cushion against the body of the wearer.

6. A system for applying pulsating pressure to the leg for stimulating fluid flow and to thereby reduce the likelihood of venous thrombosis, said system comprising a. a stocking including a seamless knitted leg portion fashioned to generally conform to the configuration of the leg on which said stocking is to be placed, said seamless knitted leg portion being sufficiently stretchable to permit easy placement and removal but being otherwise substantially unstretchable, b. a seamless knitted foot portion adapted to cover the foot and toes of the wearer, c. a longitudinally extending pocket in said leg portion of said stocking and extending from at least adjacent the ankle of the wearer to a position immediately below the knee, d. expandable bladder means generally conforming to the size of said pocket and positioned within said pocket, and e. means for periodically expanding said bladder to exert direct pressure against the portion of the leg covered thereby and to circumferentially contract the remaining corresponding portion of said leg portion to stimulate the fluid flow in the corresponding portion of the leg.

7. A system according to claim 6 wherein said longitudinally extending pocket includes an outer layer formed by said seamless knitted leg portion, an inner layer comprising a rectangular piece of material positioned inside of said seamless knitted leg portion, said rectangular piece of material being longer in the longitudinal dimension than in the widthwise dimension and with the longitudinal dimension extending longitudinally of said seamless knitted leg portion, and seam means connecting at least opposite longitudinal sides of said piece of material to said seamless knitted leg portion so that said inner layer prevents direct contact by said expandable bladder means with the corresponding portion of the body of the wearer.

8. A system according to claim 7 wherein one end of said piece of material forming said inner layer of said pocket is free of connection to said seamless knitted leg portion to permit easy placement and removal of said expandable bladder means in said pocket.

9. A system according to claim 6 wherein the width of said pocket is greater than one-fourth the circumference of said knitted leg portion but is no greater than substantially one-half the circumference of said knitted leg portion.

10. A system according to claim 6 wherein said pocket extends up the front of said seamless knitted leg portion with said pocket being centered on the front of the leg of the wearer.

11. A system according to claim 6 wherein said expandable bladder means comprises first and second layers of impervious plastic sheet material heat sealed together along their outer peripheral edges, and fluid inlet means communicating with the space between said layers of plastic sheet material, said fluid inlet means being communicatively connected with said means (d) for permitting periodic expansion of said bladder.

12. A system according to claim 7 wherein said rectangular piece of material forming said inner layer of said pocket is knitted and includes terry loops extending inwardly of said seamless knitted leg portion and forming a moisture absorbing cushion against the leg of the wearer.

13. A stocking for use with a system for applying pulsating pressure to the leg of the wearer, said stocking comprising a. a seamless knitted leg portion fashioned to generally conform to the configuration of the leg on which said stocking is to be placed, said seamless knitted leg portion being sufficiently stretchable to permit easy placement and removal but being otherwise substantially unstretchable, b. a seamless knitted foot portion adapted to cover the foot and toes of the wearer, and c. a longitudinally extending pocket in said leg portion of said stocking, said pocket extending from at least adjacent the ankle of the wearer to a position immediately below the knee.

14. A stocking according to claim 13 wherein the width of said pocket is greater than one-fourth the circumference of said knitted leg portion but is no greater than substantially one-half the circumference of said knitted leg portion.

15. A stocking according to claim 13 wherein said pocket extends up the front of said seamless knitted leg portion with said pocket being centered on the front of the leg of the wearer.

16. A stocking according to claim 13 wherein said longitudinally extending pocket includes an outer layer formed by said seamless knitted leg portion, an inner layer comprising a rectangular piece of material positioned inside of said seamless knitted leg portion, said rectangular piece of material being longer in the longitudinal direction than in the widthwise direction and with the longitudinal dimension extending longitudinally of said seamless knitted leg portion, and seam means connecting at least opposite longitudinal sides of said piece of material to said seamless knitted leg portion.

17. A stocking according to claim 16 wherein one end of said rectangular piece of material forming said inner layer of said pocket is free of connection to said seamless knitted leg portion.

18. A stocking according to claim 17 wherein said rectangular piece of material forming said inner layer of said pocket is knitted and includes terry loops extending inwardly of said seamless knitted leg portion and forming a moisture absorbing cushion against the leg of the wearer.

* * * * *